US010281390B2

(12) United States Patent
Powers et al.

(10) Patent No.: US 10,281,390 B2
(45) Date of Patent: May 7, 2019

(54) USING OPTICAL COMPUTING DEVICES TO DETERMINE UNKNOWN ANALYTES (71) Applicant: Halliburton Energy Services, Inc., Houston, TX (US)

(72) Inventors: Greg Powers, Houston, TX (US); Chris Michael Jones, Houston, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 614 days.

(21) Appl. No.: 14/908,582

(22) PCT Filed: Oct. 22, 2013

(86) PCT No.: PCT/US2013/066043
§ 371 (c)(1),
(2) Date: Jan. 29, 2016

(87) PCT Pub. No.: WO2015/060816
PCT Pub. Date: Apr. 30, 2015

(65) Prior Publication Data
US 2016/0169794 A1   Jun. 16, 2016

(51) Int. Cl.
*G01N 21/27* (2006.01)
*G01N 21/85* (2006.01)
(Continued)

(52) U.S. Cl.
CPC ............ *G01N 21/27* (2013.01); *E21B 49/08* (2013.01); *G01N 21/31* (2013.01); *G01N 21/85* (2013.01); *G01V 8/10* (2013.01); *G01N 2201/12* (2013.01)

(58) Field of Classification Search
CPC ................................. G01N 21/31; E21B 49/08
(Continued)

(56) References Cited

U.S. PATENT DOCUMENTS 5,369,578 A   11/1994   Roscoe et al.
8,094,311 B2   1/2012   Uzunbajakava et al.
(Continued)

FOREIGN PATENT DOCUMENTS

WO    2015060816 A1    4/2015

OTHER PUBLICATIONS

International Search Report and Written Opinion for PCT/US2013/066043 dated Jul. 17, 2014.

*Primary Examiner* — David P Porta
*Assistant Examiner* — Abra S Fein
(74) *Attorney, Agent, or Firm* — Gilliam IP PLLC (57) ABSTRACT

Disclosed are systems and methods of using integrated computational elements to determine unknown interferents in a fluid being monitored. One method includes monitoring a fluid with an optical computing device comprising at least two integrated computational element (ICE) cores configured to optically interact with a fluid and detect a corresponding at least two characteristics of the fluid, each ICE core being designed and manufactured with reference to known spectra related to the at least two characteristics of the fluid, generating output signals corresponding to the at least two characteristics of the fluid with the optical computing device, wherein an intensity of each output signal corresponds to a concentration of the at least two characteristics of the fluid, and calculating a representative spectrum of the fluid with a signal processor based on the known spectra of the at least two characteristics and the intensity of each output signal.

20 Claims, 2 Drawing Sheets (51) Int. Cl.
  *G01N 21/31* (2006.01)
  *E21B 49/08* (2006.01)
  *G01V 8/10* (2006.01)
(58) Field of Classification Search
  USPC ........................................................ 250/256
  See application file for complete search history.

(56) References Cited

U.S. PATENT DOCUMENTS

2007/0284518 A1   12/2007   Randall
2013/0031964 A1   2/2013   Tunheim et al.
2013/0031970 A1   2/2013   Freese et al.
2013/0031971 A1   2/2013   Freese et al.

USING OPTICAL COMPUTING DEVICES TO DETERMINE UNKNOWN ANALYTES

BACKGROUND

The present disclosure relates to optical computing devices and, more particularly, to optical computing devices that use integrated computational elements to determine unknown interferents in a fluid being monitored.

Optical computing devices, also commonly referred to as "opticoanalytical devices," can be used to analyze and monitor a substance in real time. Such optical computing devices will often employ an optical processing element that optically interacts with the substance to determine quantitative and/or qualitative values of one or more physical or chemical properties of the substance. The optical element may be, for example, an integrated computational element (ICE), also known as a multivariate optical element (MOE), which is essentially an optical interference filter that can be designed to operate over a continuum of wavelengths in the electromagnetic spectrum from the UV to mid-infrared (MIR) ranges, or any sub-set of that region. Electromagnetic radiation that optically interacts with a substance is changed and filtered by the ICE so as to be readable by a detector, such that an output of the detector can be correlated to the physical or chemical property of the substance being analyzed.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to optical computing devices and, more particularly, to optical computing devices that use integrated computational elements to determine unknown interferents in a fluid being monitored.

The exemplary systems and methods described herein use optical computing devices for the real-time or near real-time monitoring of a fluid. The optical computing devices discussed herein include two or more processing elements (e.g., integrated computational elements (ICE)) that are configured to optically interact with the fluid and provide corresponding output signals having signal intensities that correlate to concentrations of particular properties or characteristics of the fluid. Using these signal intensities and the known properties of the of the ICE cores used in the optical computing devices, a representative spectrum of the fluid as a whole may be synthetically reconstructed for analysis. This may be possible since the optical computing devices are able to measure a full spectrum intensity of the fluid with the ICE cores, and the spectral or wavelength intensity of the fluid may subsequently be back-calculated to calculate the representative spectrum of the fluid.

Determining the representative spectrum of the fluid may allow for the identification of various interferents or characteristics that were not specifically being detected using the ICE cores but were nonetheless present in the fluid. For instance, the reconstructed representative spectrum of the fluid may be projected on or otherwise compared against standard spectral data to determine which interferents or characteristics may be present within the fluid being measured. From such data, qualitative and/or quantitative data regarding the unknown interferents or characteristics may also be determined.

As used herein, the term "fluid" refers to any substance that is capable of flowing, including particulate solids, liquids, gases, slurries, emulsions, powders, muds, mixtures, combinations thereof, and the like.

As used herein, the term "characteristic" refers to a chemical, mechanical, or physical property of the fluid. A characteristic of the fluid may include a quantitative value or concentration of one or more chemical constituents or compounds present within the fluid. Such chemical constituents may be referred to herein as "analytes." The term characteristic may also be used interchangeably with and otherwise referred to herein as an "interferent" which may refer to a characteristic of the fluid that is not particularly being detected but is nonetheless present within the fluid. Illustrative characteristics of a fluid that can be monitored can include, for example, chemical composition (e.g., identity and concentration in total or of individual components or compounds), phase presence (e.g., gas, oil, water, etc.), impurity content, pH, alkalinity, viscosity, density, ionic strength, total dissolved solids, salt content (e.g., salinity), porosity, opacity, bacteria content, total hardness, combinations thereof, state of matter (solid, liquid, gas, emulsion, mixtures, etc.), and the like.

As used herein, the term "flow path" refers to a route through which a fluid is capable of being transported between at least two points. In some cases, the flow path need not be continuous or otherwise contiguous between the two points. Exemplary flow paths include, but are not limited to, a flow line, a pipeline, production tubing, drill string, work string, casing, a wellbore, an annulus defined between a wellbore and any tubular arranged within the wellbore, a mud pit, a subterranean formation, etc., combinations thereof, or the like. It should be noted that the term "flow path" does not necessarily imply that a fluid is flowing therein, rather that a fluid is capable of being transported or otherwise flowable therethrough.

As used herein, the term "electromagnetic radiation" refers to radio waves, microwave radiation, infrared and near-infrared radiation, visible light, ultraviolet light, X-ray radiation and gamma ray radiation.

As used herein, the term "optically interact" or variations thereof refers to the reflection, transmission, scattering, diffraction, or absorption of electromagnetic radiation either on, though, or from one or more processing elements, a fluid, or a gas present within the fluid. Accordingly, optically interacted light refers to electromagnetic radiation that has been reflected, transmitted, scattered, diffracted, or absorbed by, emitted, or re-radiated, for example, using a processing element, but may also apply to interaction with a fluid.

The exemplary methods described herein use at least one optical computing device that is able to detect, analyze, and quantitatively measure particular characteristics of a fluid. Each optical computing device may include an electromagnetic radiation source, at least two processing elements, and at least one detector arranged to receive optically interacted light from the processing elements or the fluid. As described in more detail below, the processing elements used in the optical computing device are integrated computational elements (ICE), also known as multivariate optical elements (MOE). The electromagnetic radiation that optically interacts with the processing elements is changed so as to be readable by a detector, such that an output of the detector can be correlated to corresponding characteristics of the fluid. The output of electromagnetic radiation from the processing element can be reflected electromagnetic radiation, transmitted electromagnetic radiation, and/or dispersed electromagnetic radiation.

The optical computing device can perform calculations (analyses) in real-time or near real-time without the need for time-consuming sample processing. The detected output from the optical computing device can be a voltage or voltages that are distinctive of the magnitude or concentration of the characteristic(s) of the fluid. For example, the optical computing device can be configured to determine the concentration of an analyte and correlate the determined concentration to a characteristic of the fluid. Moreover, the optical computing device may be configured to detect as many characteristics of the fluid as desired, being limited only by the incorporation of suitable numbers of processing and detection means for each characteristic. In some embodiments, the properties of the fluid can be a combination of the properties of the analytes therein (e.g., a linear, non-linear, logarithmic, and/or exponential combination). Accordingly, the more characteristics and analytes that are detected and analyzed using the optical computing devices, the more accurately the properties of the given fluid and/or gas will be determined.

The optical computing device utilizes electromagnetic radiation to perform calculations, as opposed to the hardwired circuits of conventional electronic processors. When electromagnetic radiation interacts with a fluid, unique physical and chemical information about the fluid is encoded in the electromagnetic radiation that is reflected from, transmitted through, or radiated from the fluid. This information is often referred to as the spectral "fingerprint" of the fluid. The optical computing device is capable of extracting the information of the spectral fingerprint of multiple analytes within a fluid, and converting that information into a detectable output related to one or more characteristics of the fluid. That is, through suitable configurations of the optical computing device, electromagnetic radiation associated with a characteristic or analyte of interest of a fluid can be separated from electromagnetic radiation associated with all other components of the fluid in order to estimate the properties of the fluid in real-time or near real-time.

Figure 1:
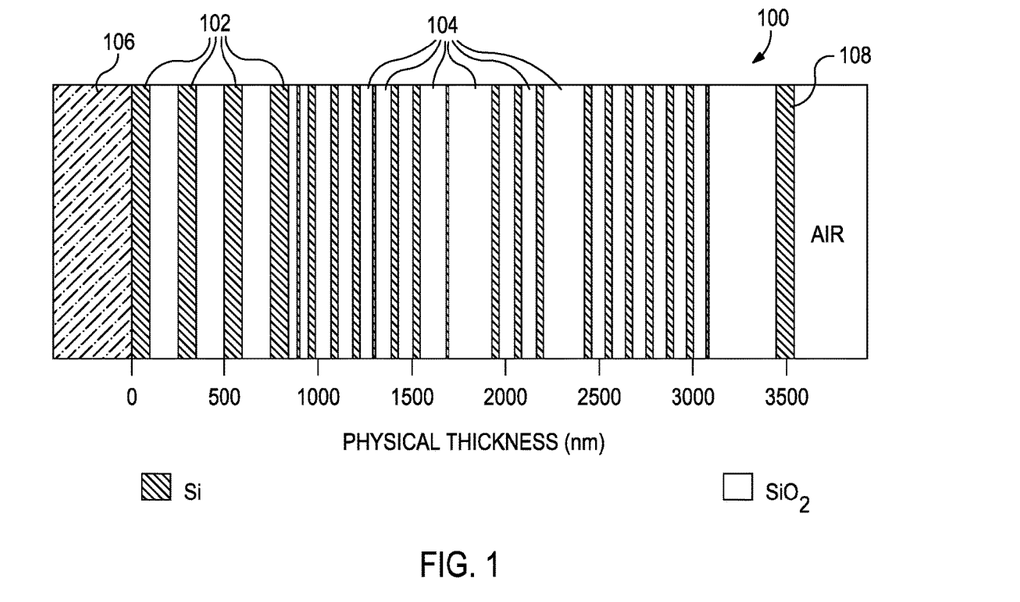
FIG. 1 illustrates an exemplary integrated computation element that may be used according to the principles presently disclosed.

As mentioned above, the processing elements used in the optical computing device may be one or more integrated computational elements (ICE). Referring to FIG. 1, illustrated is an exemplary ICE core 100. The ICE core 100 is capable of distinguishing electromagnetic radiation related to a characteristic of interest from electromagnetic radiation related to other components or constituents of a fluid. As illustrated, the ICE core 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE core 100 may include a layer 108 that is generally exposed to the environment of the device or installation. The number of layers 102, 104 and the thickness of each layer 102, 104 are determined from the spectral attributes acquired from a spectroscopic analysis of a characteristic of the fluid using a conventional spectroscopic instrument. The spectrum of interest of a given characteristic typically includes any number of different wavelengths. It should be understood that the exemplary ICE core 100 in FIG. 1 does not in fact represent any particular characteristic of a given fluid, but is provided for purposes of illustration only. Consequently, the number of layers 102, 104 and their relative thicknesses, as shown in FIG. 1, bear no correlation to any particular characteristic. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the given fluid.

In some embodiments, the material of each layer 102, 104 can be doped or two or more materials can be combined in a manner to achieve the desired optical characteristic. In addition to solids, the exemplary ICE core 100 may also contain liquids and/or gases, optionally in combination with solids, in order to produce a desired optical characteristic. In the case of gases and liquids, the ICE core 100 can contain a corresponding vessel (not shown), which houses the gases or liquids. Exemplary variations of the ICE core 100 may also include holographic optical elements, gratings, piezoelectric, light pipe, digital light pipe (DLP), and/or acousto-optic elements, for example that can create transmission, reflection, and/or absorptive properties of interest.

The multiple layers 102, 104 exhibit different refractive indices. By properly selecting the materials of the layers 102, 104 and their relative thickness and spacing, the ICE core 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE core 100 as the physical representation of the IFT. The approximations convert the IFT into a structure based on known materials with constant refractive indices.

The weightings that the layers 102, 104 of the ICE core 100 apply at each wavelength are set to the regression weightings described with respect to a known equation, or data, or spectral signature. Briefly, the ICE core 100 may be configured to perform the dot product of the electromagnetic radiation received by the ICE core 100 and a desired loaded regression vector represented by each layer 102, 104 for each wavelength. As a result, the output light intensity of the ICE core 100 will be related to the characteristic or analyte of interest.

Figure 2:
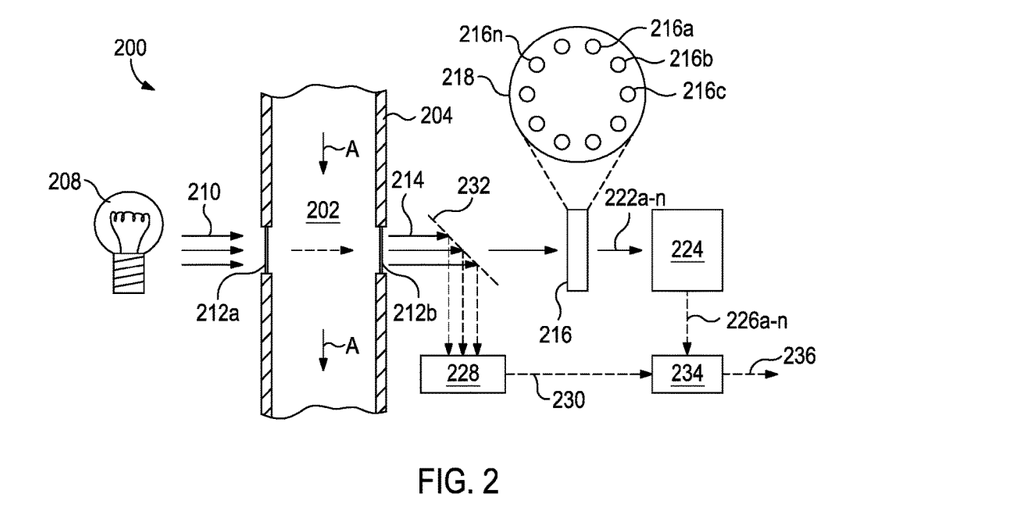
FIG. 2 illustrates an exemplary optical computing device that employs a plurality of integrated computational elements, according to one or more embodiments.

Referring now to FIG. 2, illustrated is an exemplary optical computing device 200 that may implement the principles of the present disclosure. As illustrated, the optical computing device may be arranged to monitor a fluid 202, which may be contained or otherwise flowing within an exemplary flow path 204. The flow path 204 may be a flow line, a pipeline, a wellbore, an annulus defined within a wellbore, or any flow lines or pipelines extending to/from a wellbore. The fluid 202 present within the flow path 204 may be flowing from upstream to downstream as indicated by the arrows A, but could equally be stagnant, without departing from the scope of the disclosure.

The optical computing device 200 may be configured to determine characteristics of interest in the fluid 202, such as one or more chemical compositions or analytes present within the fluid 202. In some embodiments, the device 200 may include an electromagnetic radiation source 208 configured to emit or otherwise generate electromagnetic radiation 210. The electromagnetic radiation source 208 may be any device capable of emitting or generating electromagnetic radiation 210, as defined herein. For example, the electromagnetic radiation source 208 may be a light bulb, a light emitting diode (LED), a laser, a blackbody, a photonic crystal, an X-Ray source, combinations thereof, or the like. The electromagnetic radiation 210 may be directed toward the fluid 202 and, more particularly, through the fluid 202 via a first sampling window 212a and a second sampling window 212b arranged radially-opposite the first sampling window 212a on the flow path 204. The first and second sampling windows 212a,b may be arranged adjacent to or otherwise in contact with the fluid 202 for detection purposes. The sampling windows 212a,b may be made from a variety of transparent, rigid or semi-rigid materials that are configured to allow transmission of the electromagnetic radiation 210 therethrough. For example, the sampling windows 212a,b may be made of glasses, plastics, semi-conductors, crystalline materials, polycrystalline materials, hot or cold-pressed powders, combinations thereof, or the like.

As the electromagnetic radiation 210 passes through the fluid 202 via the first and second sampling windows 212a,b, it optically interacts with the fluid 202 and optically interacted radiation 214 is subsequently generated. Those skilled in the art will readily recognize that alternative variations of the device 200 may allow the optically interacted radiation 214 to be generated by being reflected, scattered, diffracted, absorbed, emitted, or re-radiated by and/or from the fluid 202, without departing from the scope of the disclosure. The optically interacted radiation 214 generated by the interaction with the fluid 202 may be directed to or otherwise be received by a plurality of ICE cores 216 (shown as ICE cores 216a, 216b, 216c, . . . 216n) arranged within the device 200. Each ICE core 216a-n may be a spectral component substantially similar to the ICE core 100 described above with reference to FIG. 1. Accordingly, each ICE core 216a-n may be designed and otherwise configured to detect a particular and/or distinct characteristic of interest. In other embodiments, however, two or more of the ICE cores 216a-n may be configured to detect the same or substantially the same characteristic of interest.

As illustrated, the ICE cores 216a-n may be strategically arranged on a movable assembly 218, such as a rotating disc, where the ICE cores 216a-n are radially disposed for rotation therewith. In other embodiments, however, the movable assembly 218 may be a linear array (not shown) having the ICE cores 216a-n strategically arranged thereon and laterally offset from each other, without departing from the scope of the disclosure. For illustrative purposes only, and not by limitation, the movable assembly 218 will be described with reference to the rotating disc depicted in FIG. 2.

As depicted, the ICE cores 216a-n are arranged about or near the periphery of the movable assembly 218 and circumferentially-spaced from each other. In various embodiments, the movable assembly 218 may be rotated at a frequency of about 0.1 RPM to about 30,000 RPM. In operation, the movable assembly 218 may rotate such that the individual ICE cores 216a-n may each be exposed to or otherwise optically interact with the optically interacted radiation 214 for a distinct brief period of time. Upon optically interacting with the optically interacted radiation 214, each ICE core 216a-n may be configured to produce modified electromagnetic radiation 222 (shown as modified electromagnetic radiation 222a, 222b, 222c, . . . 222n) corresponding to particular characteristics of interest of the fluid 202. In particular, the modified electromagnetic radiation 222a-n is an approximation of a regression vector corresponding to the characteristic of the fluid 202 for which each ICE core 216a-n was designed to detect.

Each beam of modified electromagnetic radiation 222a-n may be directed to and detected by a detector 224, which may be configured to time multiplex the modified electromagnetic radiation 222a-n between the individually-detected beams and quantify each signal. The detector 224 may be any device capable of detecting electromagnetic radiation, and may be generally characterized as an optical transducer. In some embodiments, the detector 224 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 224 may be configured to produce individual output signals 226a-n corresponding to each beam of modified electromagnetic radiation 222a-n in real-time or near real-time. Each output signal 226a-n may be in the form of a voltage (or current) that corresponds to the particular characteristic of interest detected in the fluid 202 by each corresponding ICE core 216a-n. The output signals 226a-n returned by the detector 224 are essentially the dot product of the optical interaction of the optically interacted radiation 214 with the respective ICE cores 216a-n as a function of the concentration of the characteristic of interest of the fluid 202 that each ICE core 216a-n is configured to detect. As such, the intensity of each output signal 226a-n produced by the detector 224 and the concentration of the characteristics may be related, for example, directly proportional. In other embodiments, however, the relationship may correspond to a polynomial function, an exponential function, a logarithmic function, and/or a combination thereof.

In some embodiments, the device 200 may include a second detector 228, which may be similar to the first detector 224 in that it may be any device capable of detecting electromagnetic radiation. The second detector 228 may be used to detect radiating deviations that occur in conjunction with the intensity of the electromagnetic radiation 210 and which may cause various negative effects on the device 200. In some embodiments, radiating deviations can occur as a result of a build-up of film or material on the sampling windows 212a,b that has the effect of reducing the amount and quality of light ultimately reaching the first detector 224. Without proper compensation, such radiating deviations could result in false readings and the output signals 226a-n would no longer be primarily or accurately related to the characteristic of interest.

To compensate for these types of undesirable effects, the second detector 228 may be configured to generate a compensating signal 230 generally indicative of the radiating deviations of the electromagnetic radiation source 208, and thereby normalize the output signals 226a-n generated by the first detector 224. As illustrated, the second detector 228 may be configured to receive a portion of the optically interacted radiation 214 via a beam splitter 232 in order to detect the radiating deviations. In other embodiments, however, the second detector 228 may be arranged to receive electromagnetic radiation from any portion of the optical train in the device 200 in order to detect the radiating deviations, without departing from the scope of the disclosure. In yet other embodiments, at least one of the ICE cores 216a-n may be a neutral element configured to simply pass the optically interacted radiation 214 without optical-interaction with the movable assembly 218. As a result, the neutral element may be configured to provide a neutral signal to the detector 224 that may be substantially similar to the compensating signal 230.

In some applications, the output signals 226a-n and the compensating signal 230 may be conveyed to or otherwise received by a signal processor 234 communicably coupled to both the detectors 224, 228. The signal processor 234 may be a computer including a processor and a machine-readable storage medium having instructions stored thereon, which, when executed by the processor 234, cause the optical computing device 200 to perform a number of operations, such as determining a characteristic of interest of the fluid 202. For instance, the concentration of each characteristic detected with the optical computing device 200 can be fed into an algorithm operated by the signal processor 234. The algorithm can be part of an artificial neural network configured to use the concentration of each detected characteristic in order to evaluate the overall characteristic(s) or quality of the fluid 202.

The signal processor 234 may also be configured to computationally combine the compensating signal 230 with the output signals 226a-n in order to normalize the output signals 226a-n in view of any radiating deviations detected by the second detector 228. Computationally combining the output and compensating signals 226, 230 may entail computing a ratio of the two signals 226, 230. For example, the concentration or magnitude of each characteristic determined using the optical computing device 200 can be fed into an algorithm run by the signal processor 234. In real-time or near real-time, the signal processor 234 may be configured to provide a resulting output signal 236 corresponding to the characteristics of interest in the fluid 202. In some embodiments, the resulting output signal 236 may be conveyed, either wired or wirelessly, to an operator for consideration.

It should be noted that, while FIG. 2 depicts the movable assembly 218 as receiving the optically interacted radiation 214 as transmitted through the sampling windows 212a,b, the movable assembly 218 may equally be arranged at any point along the optical train of the device 200, without departing from the scope of the disclosure. For example, in one or more embodiments, the movable assembly 218 may be arranged within the optical train prior to the first sampling window 212a and equally obtain substantially the same results. In yet other embodiments, the ICE cores 216a-n may generate the modified electromagnetic radiation 222 through reflection, instead of transmission therethrough.

Accordingly, the optical computing device 200 may be able to monitor the fluid 202 and detect and report the concentration of characteristics corresponding to the design and manufacture of each ICE core 216a-n. It will be appreciated that any number of ICE cores 216a-n may be used in the device 200, thereby providing data corresponding to an equal number of characteristics of the fluid 202.

Instead of actually collecting an optical spectrum of the fluid 202 being monitored, each ICE core 216a-n performs an optical analysis that provides an analyte concentration from a corresponding optical regression vector. More specifically, as discussed above with reference to FIG. 1, the weightings of the layers of each ICE core 216a-n may be designed to correspond to the regression weightings associated with the spectral signature of a particular analyte or characteristic. As known to those in the art, such spectral signatures can be derived from commercially-available spectral libraries or from experimentally-measured spectra that may be available. During operation, each ICE core 216a-n performs the dot product between the optically interacted radiation 214 and the desired loaded regression vector represented by each layer 102, 104 for each wavelength. The intensity of each resulting output signal 226a-n from each ICE core 216a-n is then related to or otherwise proportional to the concentration of the characteristic or analyte of interest in the fluid 202. This relationship can be described mathematically as follows:

$$C_n \propto X \cdot B_n \quad \text{Equation (1)}$$

where $C_n$ is the concentration of the analytes or characteristics being measured by "n" number of ICE cores (i.e., ICE cores 216a-n), X is the fluid 202 being monitored, and $B_n$ is the transmission spectra of "n" number of ICE cores. Accordingly, the scalar product of the transmission spectra ($B_n$) derived from the ICE cores 216a-n and the optically interacted radiation 214 from the fluid 202 is proportional to the concentration ($C_n$) of those analytes or characteristics present in the fluid 202.

According to the present disclosure, the calculation and determination of a spectrum relating to an unknown characteristic or "interferent" may be obtained from the output signals of at least two of the ICE cores 216a-n. To do this, the resulting scalar products, or intensities of the output signals 226a-n from each ICE core 216a-n, may be used to interpret data from the fluid 202 for which the ICE cores 216a-n were not necessarily designed for. As a result, the responses from multiple ICE cores 216a-n may be used to generate a representative spectrum of the fluid 202 that may be analyzed either in situ in realtime or otherwise during post-job analysis.

To accomplish this, the optical computing device 200 may be operated as generally discussed above to obtain various measurements of the fluid 202 using the ICE cores 216a-n. Within the fluid 202 may be one or more interferents or characteristics of interest that the ICE cores 216a-n are not designed or otherwise configured to detect. A corresponding number of output signals 226a-n are generated from the ICE cores 216a-n and recorded following optical interaction with the optically interacted radiation 214. The intensity of each output signal 226a-n from each ICE core 216a-n corresponds to the concentration of the characteristic or analyte of interest that it was designed to detect in the fluid 202. This relationship can be described mathematically as follows:

$$I_n = X \cdot B_n \quad \text{Equation (2)}$$

where $I_n$ is the signal intensity measured by each ICE core 216a-n, X is the actual or true spectrum of the fluid 202 as a whole being measured (i.e., a "representative spectrum" of the fluid 202), and $B_n$ is the actual transmission spectra of the ICE cores 216a-n used in the device 200.

As obtained and recorded by the detector 224, the signal intensities ($I_n$), which are inherently eigenvalues, are now known voltages (or current) that can be correlated to the concentration of the corresponding characteristics being measured by each ICE core 216a-n. Moreover, the actual transmission spectra ($B_n$) of the ICE cores 216a-n is also known since each ICE core 216a-n was designed and manufactured in accordance with and with reference to a known spectral fingerprint of a particular characteristic of interest. As a result, the design of each ICE core 216a-n was predetermined and set to eigenvectors of a known spectrum. Accordingly, two of the three variables from Equation (2) are now known, and solving for (X) may provide a representative spectrum (i.e., a pseudo-spectrum) of the fluid 202 that is being monitored, including spectra relating to any unknown interferents and characteristics of interest that may be present therein.

The representative spectrum (X) may be determined or otherwise calculated using a computer system, such as the signal processor 234 depicted in FIG. 2 or another computer system that may be in communication with the optical computing device 200. In some embodiments, the representative spectrum (X) may be mathematically determined by inverting the known eigenvectors of the predetermined actual transmission spectra ($B_n$) for each ICE core 216a-n with respect to the known eigenvalue signal intensities ($I_n$) measured by each ICE core 216a-n. In other embodiments, the representative spectrum (X) may be mathematically determined by using an iterative alternating partial least squares method or the like. Those skilled in the art will readily appreciate that any mathematical means or processes may be applied to Equation (2) in order to generate or otherwise determine the representative spectrum (X) for the fluid 202, without departing from the scope of the disclosure.

Once the representative spectrum (X) is determined or otherwise calculated, several features of the fluid 202 may be ascertained and analyzed. For instance, the representative spectrum (X) may then be projected onto or otherwise compared against known or standard spectra found in spectral libraries or experimentally-measured spectra that may be available. The standard spectra are spectra corresponding to standard analytes, chemical compositions, or characteristics of natural and/or man-made substances. As with the calculation of the representative spectrum (X), this may be done using a computer system, such as the signal processor 234 of FIG. 2, for example. Comparing the representative spectrum (X) against standard spectra may allow for the identification of one or more unknown interferents or characteristics of interest present in the fluid 202. In the event that the representative spectrum (X) fails to match a standard spectrum, a difference between the representative spectrum (X) and a standard spectrum (or standard spectra) may be determined. The difference obtained may correspond to (or closely match) one or more of the unknown interferents or characteristics of interest present in the fluid 202.

This projection and post-processing of the representative spectrum (X) may then provide for either quantitative or qualitative analysis of properties relating to the unknown interferents or characteristics of interest. Again, for qualitative analysis, a library search of the difference between the representative spectrum (X) and a standard spectrum (Y) yields a difference spectrum (Z). The difference spectrum Z is a qualitative representation for an interferent. A spectral library search can be made to locate and otherwise identify a match for the difference spectrum Z. In other cases, especially where an exact spectral match between the difference spectrum Z and a standard spectrum Y is unavailable or otherwise not identified, a mathematical algorithm or computer program may be used or otherwise implemented to undertake a correlation analysis to a closest match to an interferent. With respect to quantitative analysis, the Beer-Lambert law shows how individual components in a sample, each with unique spectral profiles, will add linearly to generate a representative spectrum X. Thus, the magnitude of the difference spectrum Z can be determined and otherwise used to quantify how much of an interferent is present in the representative spectrum X.

Referring still to FIG. 2, such calculations and determinations with respect to the representative spectrum (X) may be done in situ, while the device 200 is downhole. More particularly, the signal processor 234 may include an algorithm configured to calculate the representative spectrum (X). The signal processor 234 may further include onboard memory having stored thereon standard spectral data that may be queried and otherwise accessed in order to compare the representative spectrum (X) thereto. As a result, the unknown interferents or characteristics may be ascertained in real-time while the device 200 is downhole. The results of such determinations may be conveyed, either wired or wirelessly, to an operator at the surface in the form of the resulting output signal 236 for consideration. For instance, in some embodiments, the device 200 may be communicably coupled to a surface location via one or more wires, fiber optic cables, or the like. Likewise, the device 200 may configured to communicate with a surface location via wireless telemetry methods, such as electromagnetic, acoustic, or mud pulse telemetry methods.

Because of the real-time capabilities of this technology, the device 200 may continuously monitor the fluid 202 during various downhole operations and simultaneously transmit resulting output signals 236 to the surface for consideration. In other embodiments, however, such determinations may be stored in onboard memory included in the signal processor 234 and accessed by an operator upon returning the device 200 to the surface for post-job analysis.

Figure 3:
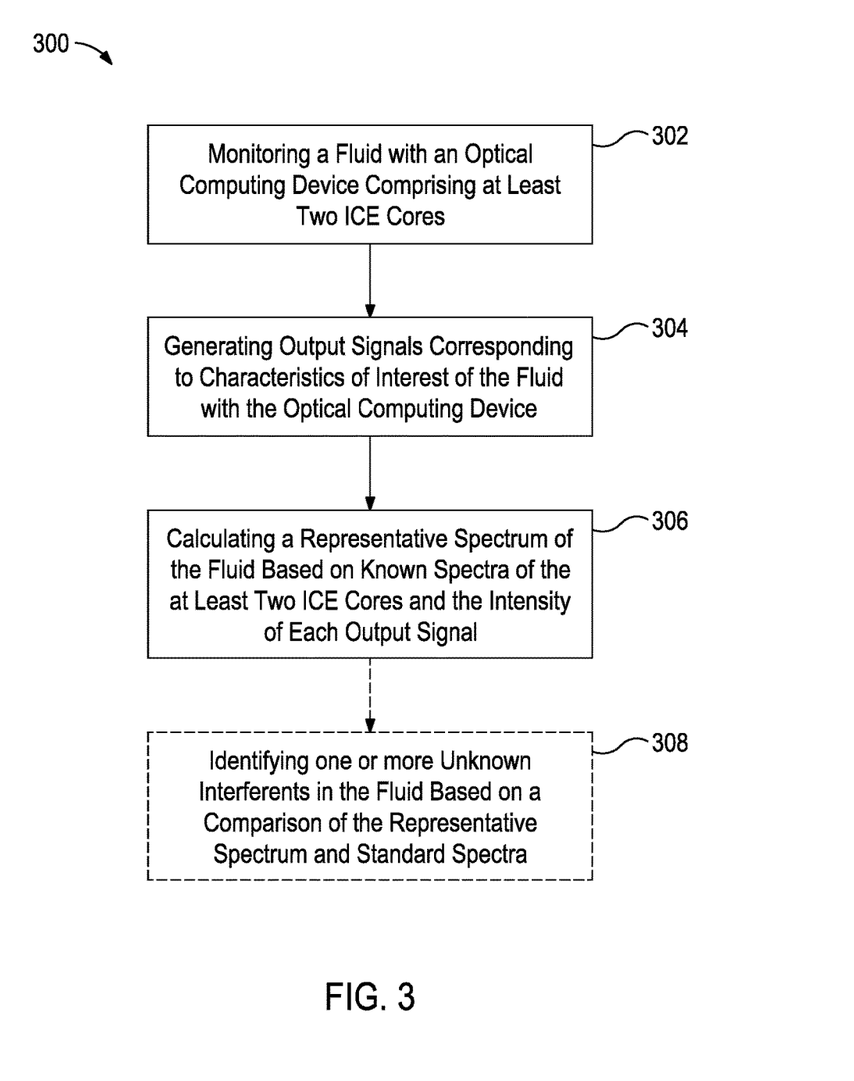
FIG. 3 depicts a schematic flowchart of a method in accordance to the principles of the present disclosure.

Referring now to FIG. 3, illustrated is a schematic flowchart of a method 300 in accordance to the principles of the present disclosure. As illustrated, the method 300 may include monitoring a fluid with an optical computing device comprising at least two ICE cores, as at 302. Each ICE core may be configured to detect corresponding characteristics of interest of the fluid. Moreover, each ICE core may be designed and manufactured with reference to known spectra related to their corresponding characteristics of interest of the fluid. Output signals corresponding to the characteristics of the fluid may then be generated with the optical computing device, as at 304. The intensity of each output signal may correspond to a concentration of the characteristics of the fluid being detected by the at least two ICE cores. The method 300 may also include calculating a representative spectrum of the fluid based on the known spectra of the at least two characteristics and the intensity of each output signal, as at 306. The representative spectrum may be calculated with a computer system, such as a signal processor associated with the optical computer device.

In some embodiments, the method 300 may further include identifying one or more unknown interferents present in the fluid based on a comparison of the representative spectrum against standard spectra, as at 308. More particularly, a spectral library may be queried by the computer system to search for standard spectra, and the representative spectrum may then be compared against the standard spectra found in the spectral library.

Those skilled in the art will readily recognize that it is possible to generate two different regression vectors from two individual ICE cores for the same analyte or characteristic being detected. Agreement of the result from these two different regression vectors may provide assurances that there are no inteferents in the fluid being monitored, since an inteferent would likely not affect the two regression vectors of sufficient rank in the same way. If, however, the two regression vectors yield different results, then it may be surmised that there is at least one uncharacterized inteferent present within the fluid. The regression vector responses of the two individual ICE cores of sufficient rank may be used to back calculate and determine which inteferent(s) is/are present within the fluid. As will be appreciated, more ICE cores used to accomplish this will provide results that are more accurate.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. A method of monitoring a fluid with an optical computing device comprising at least two integrated computational element (ICE) cores configured to optically interact with a fluid and detect a corresponding at least two characteristics of the fluid, each ICE core being designed and manufactured with reference to known spectra related to the at least two characteristics of the fluid, generating output signals corresponding to the at least two characteristics of the fluid with the optical computing device, wherein an intensity of each output signal corresponds to a concentration of the at least two characteristics of the fluid, and calculating a representative spectrum of the fluid with a signal processor based on the known spectra of the at least two characteristics and the intensity of each output signal.

B. A system that includes a flow path containing a fluid, at least two integrated computational element (ICE) cores configured to optically interact with the fluid and generate modified electromagnetic radiation corresponding to a corresponding at least two characteristics of the fluid, each ICE core being designed and manufactured with reference to known spectra related to the at least two characteristics of the fluid, at least one detector arranged to receive the modified electromagnetic radiation and generate output signals corresponding to the at least two characteristics of the fluid, wherein an intensity of each output signal corresponds to a concentration of the at least two characteristics of the fluid, and a signal processor configured to calculate a representative spectrum of the fluid based on the known spectra of the at least two characteristics and the intensity of each output signal.

C. A non-transitory computer readable medium including computer readable instructions stored thereon which, when executed by a processor, configure the processor to perform functions that include monitoring a fluid with an optical computing device comprising at least two integrated computational element (ICE) cores configured to optically interact with a fluid and detect a corresponding at least two characteristics of the fluid, each ICE core being designed and manufactured with reference to known spectra related to the at least two characteristics of the fluid, generating output signals corresponding to the at least two characteristics of the fluid with the optical computing device, wherein an intensity of each output signal corresponds to a concentration of the at least two characteristics of the fluid, and calculating a representative spectrum of the fluid with a signal processor based on the known spectra of the at least two characteristics and the intensity of each output signal.

Each of embodiments A, B, and C may have one or more of the following additional elements in any combination: Element 1: further comprising querying a spectral library for standard spectra, comparing the representative spectrum against the standard spectra, and identifying one or more unknown interferents present in the fluid based on a comparison of the representative spectrum against the standard spectra. Element 2: further comprising determining a difference between the representative spectrum and one or more of the standard spectra, and identifying one or more of the unknown interferents present in the fluid based on the difference. Element 3: wherein calculating a representative spectrum of the fluid with the signal processor further comprises inverting eigenvectors of the known spectra related to the at least two characteristics with respect to the eigenvalues corresponding to the intensity of each output signal. Element 4: wherein calculating a representative spectrum of the fluid further comprises receiving the output signals corresponding to the at least two characteristics of the fluid with the signal processor, querying a spectral library with the signal processor to obtain the known spectra related to the at least two characteristics, and inverting the intensity of the output signals with respect to the known spectra. Element 5: wherein the at least two ICE cores are arranged on a movable assembly, the method further comprising moving the movable assembly such that the at least two ICE cores optically interact with the fluid a distinct period of time, producing corresponding beams of modified electromagnetic radiation from each ICE core, the modified electromagnetic radiation being an approximation of a regression vector corresponding to the at least two characteristics of the fluid, receiving the corresponding beams of modified electromagnetic radiation with a detector, and generating the output signals with the detector. Element 6: wherein monitoring the fluid comprises monitoring the fluid as the fluid flows within a flow path. Element 7: further comprising deploying the optical computing device downhole in a wellbore and calculating the representative spectrum in situ downhole. Element 8: further comprising conveying the representative spectrum of the fluid to a surface location. Element 9: further comprising storing the representative spectrum in memory associated with the optical computing device, returning the optical computing device to a surface location, and obtaining the representative spectrum from the memory at the surface location.

Element 10: further comprising a spectral library containing standard spectra, wherein the representative spectrum is compared against the standard spectra with the signal processor to identify one or more unknown interferents present in the fluid. Element 11: wherein a difference between the representative spectrum and one or more of the standard spectra is determined by the signal processor in order to identify one or more of the unknown interferents present in the fluid. Element 12: further comprising a movable assembly, wherein the at least two ICE cores are arranged on the movable assembly and configured to move therewith.

Element 13: further comprising querying a spectral library for standard spectra, comparing the representative spectrum against the standard spectra, and identifying one or more unknown interferents present in the fluid based on a comparison of the representative spectrum against the standard spectra. Element 14: further comprising determining a difference between the representative spectrum and one or more of the standard spectra, and identifying one or more of the unknown interferents present in the fluid based on the difference. Element 15: wherein calculating a representative spectrum of the fluid with the signal processor further comprises inverting eigenvectors of the known spectra related to the at least two characteristics with respect to the eigenvalues corresponding to the intensity of each output signal. Element 16: wherein calculating a representative spectrum of the fluid further comprises receiving the output signals corresponding to the at least two characteristics of the fluid with the signal processor, querying a spectral library with the signal processor to obtain the known spectra related to the at least two characteristics, and inverting the intensity of the output signals with respect to the known spectra. Element 17: wherein the at least two ICE cores are arranged on a movable assembly, the method further comprising moving the movable assembly such that the at least two ICE optically interact with the fluid for a distinct period of time, producing corresponding beams of modified electromagnetic radiation from each ICE core, the modified electromagnetic radiation being an approximation of a regression vector corresponding to the at least two characteristics of the fluid, receiving the corresponding beams of modified electromagnetic radiation with a detector, and generating the output signals with the detector.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:
1. A method, comprising:
monitoring a fluid with an optical computing device comprising at least two integrated computational element (ICE) cores configured to optically interact with a fluid and detect a corresponding at least two characteristics of the fluid, each ICE core being designed and manufactured with reference to known spectra related to the at least two characteristics of the fluid;

generating output signals corresponding to the at least two characteristics of the fluid with the optical computing device, wherein an intensity of each output signal corresponds to a concentration of the at least two characteristics of the fluid; and calculating a representative spectrum of the fluid with a signal processor based on the known spectra of the at least two characteristics and the intensity of each output signal.

2. The method of claim 1, further comprising:
querying a spectral library for standard spectra;
comparing the representative spectrum against the standard spectra; and
identifying one or more unknown interferents present in the fluid based on a comparison of the representative spectrum against the standard spectra.

3. The method of claim 2, further comprising:
determining a difference between the representative spectrum and one or more of the standard spectra; and
identifying one or more of the unknown interferents present in the fluid based on the difference.

4. The method of claim 1, wherein calculating a representative spectrum of the fluid with the signal processor further comprises inverting eigenvectors of the known spectra related to the at least two characteristics with respect to the eigenvalues corresponding to the intensity of each output signal.

5. The method of claim 1, wherein calculating a representative spectrum of the fluid further comprises:
receiving the output signals corresponding to the at least two characteristics of the fluid with the signal processor;
querying a spectral library with the signal processor to obtain the known spectra related to the at least two characteristics; and
inverting the intensity of the output signals with respect to the known spectra.

6. The method of claim 1, wherein the at least two ICE cores are arranged on a movable assembly, the method further comprising:
moving the movable assembly such that the at least two ICE cores optically interact with the fluid a distinct period of time;
producing corresponding beams of modified electromagnetic radiation from each ICE core, the modified electromagnetic radiation being an approximation of a regression vector corresponding to the at least two characteristics of the fluid;
receiving the corresponding beams of modified electromagnetic radiation with a detector; and
generating the output signals with the detector.

7. The method of claim 1, further comprising deploying the optical computing device downhole in a wellbore and calculating the representative spectrum in situ downhole.

8. The method of claim 7, further comprising conveying the representative spectrum of the fluid to a surface location.

9. The method of claim 7, further comprising:
storing the representative spectrum in memory associated with the optical computing device;
returning the optical computing device to a surface location; and
obtaining the representative spectrum from the memory at the surface location.

10. The method of claim 1, wherein the corresponding at least two characteristics of the fluid are the same characteristic of the fluid.

11. A system, comprising:
a flow path containing a fluid;
at least two integrated computational element (ICE) cores configured to optically interact with the fluid and generate modified electromagnetic radiation corresponding to a corresponding at least two characteristics of the fluid, each ICE core being designed and manufactured with reference to known spectra related to the at least two characteristics of the fluid;
at least one detector arranged to receive the modified electromagnetic radiation and generate output signals corresponding to the at least two characteristics of the fluid, wherein an intensity of each output signal corresponds to a concentration of the at least two characteristics of the fluid; and
a signal processor configured to calculate a representative spectrum of the fluid based on the known spectra of the at least two characteristics and the intensity of each output signal.

12. The system of claim 11, further comprising a spectral library containing standard spectra, wherein the representative spectrum is compared against the standard spectra with the signal processor to identify one or more unknown interferents present in the fluid.

13. The system of claim 12, wherein a difference between the representative spectrum and one or more of the standard spectra is determined by the signal processor in order to identify one or more of the unknown interferents present in the fluid.

14. The system of claim 11, further comprising a movable assembly, wherein the at least two ICE cores are arranged on the movable assembly and configured to move therewith.

15. A non-transitory computer readable medium including computer readable instructions stored thereon which, when executed by a processor, configure the processor to perform functions including:
monitoring a fluid with an optical computing device comprising at least two integrated computational element (ICE) cores configured to optically interact with a fluid and detect a corresponding at least two characteristics of the fluid, each ICE core being designed and manufactured with reference to known spectra related to the at least two characteristics of the fluid;
generating output signals corresponding to the at least two characteristics of the fluid with the optical computing device, wherein an intensity of each output signal corresponds to a concentration of the at least two characteristics of the fluid; and
calculating a representative spectrum of the fluid with a signal processor based on the known spectra of the at least two characteristics and the intensity of each output signal.

16. The non-transitory computer readable medium of claim 15, further comprising:
querying a spectral library for standard spectra;
comparing the representative spectrum against the standard spectra; and
identifying one or more unknown interferents present in the fluid based on a comparison of the representative spectrum against the standard spectra.

17. The non-transitory computer readable medium of claim 16, further comprising:
determining a difference between the representative spectrum and one or more of the standard spectra; and identifying one or more of the unknown interferents present in the fluid based on the difference.

18. The non-transitory computer readable medium of claim 15, wherein calculating a representative spectrum of the fluid with the signal processor further comprises inverting eigenvectors of the known spectra related to the at least two characteristics with respect to the eigenvalues corresponding to the intensity of each output signal.

19. The non-transitory computer readable medium of claim 15, wherein calculating a representative spectrum of the fluid further comprises:
   receiving the output signals corresponding to the at least two characteristics of the fluid with the signal processor;
   querying a spectral library with the signal processor to obtain the known spectra related to the at least two characteristics; and
   inverting the intensity of the output signals with respect to the known spectra.

20. The non-transitory computer readable medium of claim 15, wherein the at least two ICE cores are arranged on a movable assembly, the method further comprising:
   moving the movable assembly such that the at least two ICE optically interact with the fluid for a distinct period of time;
   producing corresponding beams of modified electromagnetic radiation from each ICE core, the modified electromagnetic radiation being an approximation of a regression vector corresponding to the at least two characteristics of the fluid;
   receiving the corresponding beams of modified electromagnetic radiation with a detector; and
   generating the output signals with the detector.

* * * * *